United States Patent [19]

Beck et al.

[11] Patent Number: 4,893,270

[45] Date of Patent: Jan. 9, 1990

[54] MEDICAL INFORMATION SYSTEM

[75] Inventors: Roger P. Beck, Reynoldsburg; Daniel L. Castagno, Pickerington; Robert B. Craig, Jr., Westerville; Timothy S. Davidheiser, Reynoldsburg; Allen W. Haley, Jr., Columbus; Stanley M. Huff, Westerville; Russell P. Radigan, Johnstown, all of Ohio

[73] Assignee: American Telephone and Telegraph Company, AT&T Bell Laboratories, Murray Hill, N.J.

[21] Appl. No.: 862,094

[22] Filed: May 12, 1986

[51] Int. Cl.⁴ ..................... G06F 15/16; G06F 15/42
[52] U.S. Cl. ..................... 364/900; 364/922; 364/940.81; 364/933.9
[58] Field of Search ... 364/200 MS File, 900 MS File

[56] References Cited

U.S. PATENT DOCUMENTS

| | | | |
|---|---|---|---|
| 3,668,699 | 6/1972 | Pedersen et al. | 364/900 |
| 3,872,448 | 3/1975 | Mitchell, Jr. | 364/900 |
| 3,898,373 | 8/1975 | Walsh | 364/900 |
| 4,091,448 | 5/1978 | Clausing | 364/200 |
| 4,200,930 | 4/1980 | Rawlings et al. | 364/200 |
| 4,281,315 | 7/1981 | Bauer et al. | 364/200 |
| 4,388,683 | 6/1983 | Beifuss et al. | 364/200 |
| 4,434,460 | 2/1984 | Drakenborn et al. | 364/200 |
| 4,438,326 | 3/1984 | Uchida | 364/900 |
| 4,486,828 | 12/1984 | Kitamura et al. | 364/200 |
| 4,489,387 | 12/1984 | Lamb et al. | 364/514 |
| 4,513,373 | 4/1985 | Sheets | 364/200 |
| 4,516,200 | 5/1985 | Thompson | 364/200 |
| 4,591,974 | 5/1986 | Dornbush et al. | 364/200 |
| 4,648,061 | 3/1987 | Foster | 364/900 |

Primary Examiner—Gareth D. Shaw
Assistant Examiner—Debra A. Chun
Attorney, Agent, or Firm—Dwight A. Marshall

[57] ABSTRACT

A medical information system (1) for use in a hospital environment. The system comprises clinic and department computer terminals (1000) of the hospital interconnected with a message network (19). A computer terminal (10010, 10011, 10022) is arranged to enter record and medical data into the system. The record and medical data is formatted (10017, 10018) into a data message and transmitted over the message network to each of the other computer terminals. Each computer terminal modifies (10015, 10017, 10018) the received record and medical data in accordance with clinic and departmental station requirements file data (10015) assigned the receiving computer terminal and records (10011, 10018, 10022) the modified record and medical data in forms files and medical data dictionary data bases (100112, 100222). Patient data entered into the clinic and department computer terminals is recorded in a computer terminal patient file data base (10030) consistent with the modified record and medical data recorded in the computer terminal forms files and medical data dictionary data bases.

16 Claims, 5 Drawing Sheets

MEDICAL INFORMATION SYSTEM

TECHNICAL FIELD

This invention relates to an information system. In particular, it relates to a medical information system.

BACKGROUND OF THE INVENTION

Today's hospitals generally have a large number of clinics and departments that serve both the patients and the needs of the hospital. A patient entering a hospital may be admitted by the registration department or through an emergency care unit and assigned a room in a hospital in-patient clinic. Later, the admitted patient may undergo a series of tests that involve the hospital laboratories and specimens may be taken to determine the state of the patient's health. The patient may, depending on the results of the tests, undergo surgery and spend time in a recovery room or intensive care unit under the constant care of physicians and nursing staff.

The patient, after leaving the recovery room or intensive care unit, may be returned to the originally assigned room or to a room in another in-patient clinic of the hospital. Personal physicians of the patient, along with staff physicians and nurses of the hospital, may prescribe various tests and drugs required for care of the patient. Record entries for the patient are maintained at the in-patient clinic nurses station. Various medicines and drugs are obtained from the hospital pharmacy and charge information provided to the hospital financial department. The financial department accumulates patient charges and prepares a bill that is available at the financial department upon discharge of the patient from the hospital.

In addition to the hospital in-patient clinic, there may be out-patient clinics where a patient may be admitted for the purpose of receiving hospital services performed by physicians and nurses. As with the in-patient clinics, the out-patient clinics may prescribe tests and obtain medicines and drugs from the hospital pharmacy. Record entries are prepared and used by the physicians and nurses to provide care for the patient and by the financial department in preparing a bill for services. In addition, there may be a hospital records department where records of current patients are maintained and records of past patients are archived. Hospitals also have medical departments wherein patient records may be maintained by various physicians and wherein new medical record forms may be developed. In addition, new drugs and medical procedures may be recommended by the medical department for use by the hospital physician and nursing staff.

Information systems have been developed for hospitals for use by the hospital financial department in preparing patient bills. Such a type of information system is usually provided on a large mainframe computer which is also used for general financial matters such as payroll, accounts receivable and accounts payable. In addition, a hospital may also have a medical claim verification and processing system for determining a patient's background, medical and insurance information for use in determining the amount of payment for particular insurance claims. Some hospitals may also have a computer-controlled medical care system for use in the treatment and care of patients. Such systems have a control unit adapted for instructing through algorithms teams of hospital staff physicians and nurses and advising the team members to perform diagnostic and therapeutic procedures according to a predetermined plan. There may also be a computer-controlled medical system for use in caring for the needs of specific patients and for receiving, storing and reporting medical test information for an entire patient population.

A problem arises in that each of these information systems are a stand-alone system developed for use by a specific clinic or department of a hospital. It appears that none of these systems have been developed for use by all of the clinics and departments of a hospital. Accordingly, a need exists for a medical information system interconnecting all of the clinics and departments of a hospital. A need also exists for a hospital information system interconnecting all of the clinics and departments of a hospital wherein record and medical data may be entered into the system and made available to all of the clinics and departments of a hospital in accordance with specific clinic and department station requirements required to protect record, medical and patient data.

SUMMARY OF THE INVENTION

The foregoing problems are solved and a technical advantage is achieved by an information system having interconnected user groups of computer terminals each provided with a user protocol for use in conditioning each computer terminal in recording data at the computer terminal in accordance with the user class and user protocol.

In accordance with the invention, a medical information system having interconnected computer terminals has apparatus for entering record and medical data into one of the computer terminals and recording the entered record and medical data in forms files and medical data dictionary data bases of the computer terminal. The computer terminal apparatus is arranged to access the recorded record and medical data at predetermined intervals of time and transmit the record and medical data to each of the interconnected computer terminals. Each computer terminal modifies the received record and medical data in accordance with station requirement data assigned the computer terminal. The modified record and medical data is recorded in the computer terminal forms files and medical data dictionary data bases for use in entering patient data into a patient data base of the computer terminal consistent with the recorded modified record and medical data.

Also in accordance with the invention, a medical information system having interconnected computer terminals is arranged for transmitting updated record and medical data to each of the computer terminals for use in recording patient data. Visual editor apparatus common to each of the computer terminals is arranged for entering the record and medical data into the computer terminal and for verifying the accuracy of the entered record and medical data.

Also in accordance with the invention, a medical information system having interconnected computer terminals arranged for entering record and medical data into each computer terminal has apparatus for formatting the entered record and medical data into a record and medical data message for transmission to each computer terminal at predetermined intervals of time.

Also in accordance with the invention, a medical information system has interconnected computer terminals with each having station requirement data assigned thereto and each arranged to receive record and medical data messages from another of the computer terminals. The computer terminals are arranged to modify the received record and medical data in accordance with the station requirement data and record the modified record and medical data in a forms files data base and medical data dictionary data base of the receiving computer terminal. Patient data entered into each computer terminal is recorded into a patient file data base of the receiving computer terminal consistent with the station requirement modified record and medical data recorded in the receiving computer terminal forms files and medical data dictionary data bases.

In further accordance with the invention, a method of enabling a hospital medical information system having a medical department master computer terminal and clinic and department computer terminals each interconnected with a message network is arranged for conditioning the clinic and department computer terminals to accept patient data. The method comprises the steps of entering record and medical data into the medical department master computer terminal and verifying the accuracy of the entered record and medical data. The verified record and medical data is recorded in a forms files data base and medical data dictionary data base, respectively, of the medical department master computer terminal. The method also comprises the steps of accessing the medical department master computer terminal forms files and medical data dictionary data bases and formatting the entered and verified record and medical data into record and medical data messages. The method further comprises the steps of transmitting the formatted record and medical data messages over the message network to each clinic and departmental computer terminal connected to the message network and receiving the transmitted record and medical data messages at each clinic and departmental computer terminal. The received record and medical data is modified in accordance with clinical and departmental data assigned each receiving clinic and departmental computer terminal and recorded in a forms files data base and medical data dictionary data base, respectively, of the receiving clinic and departmental computer terminal. The method also comprises the steps of entering patient data into each receiving clinic and departmental computer terminal and recording the entered patient data in a patient file data base of the receiving clinic and departmental computer terminal consistent with the modified record and medical data recorded in the receiving clinic and department computer terminal forms files and medical data dictionary data bases.

BRIEF DESCRIPTION OF THE DRAWING

The foregoing as well as other objects, features and advantages of the invention will be more apparent from a description of the drawing in which.

DESCRIPTION OF THE INVENTION

Figure 1:
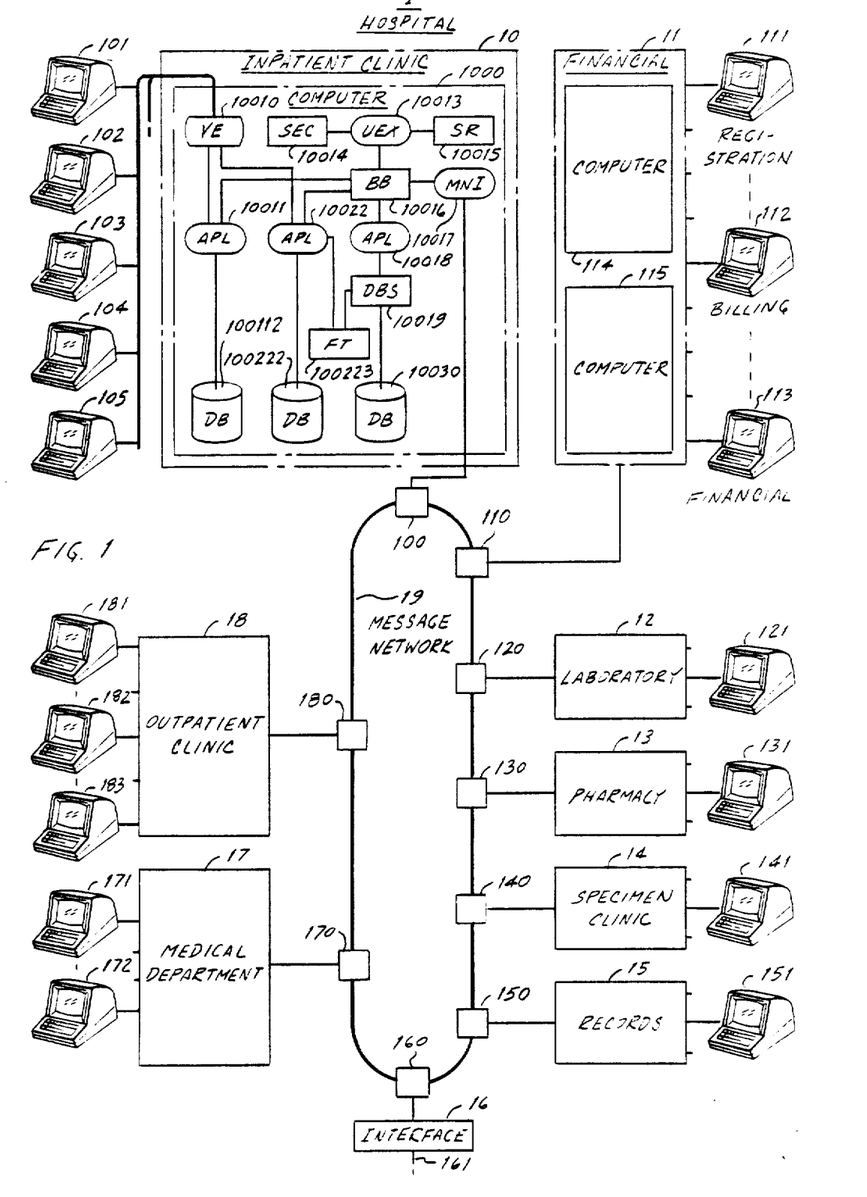
FIG. 1 is a block diagram of a medical information system embodying the principles of the invention.

Referring to the drawing and more specifically to FIG. 1 of the drawing, hospital information system 1 set forth therein is intended for use in interconnecting various clinics and departments of a hospital in order to share common information modified to clinical and departmental station requirements defined by each computer terminal. For example, hospital financial department 11 may have several minicomputers 114, 115 or a large mainframe computer serving several work areas that may have registration computer terminals 111, billing computer terminals 112 or hospital financial record computer terminals 113. Financial department computer terminals 111, 112, 113 are interconnected through financial department computers 114, 115 with financial node 110 of interconnection message network 19. Message network 19 may be any one of several different types of networks commonly referred to as local area types of packet networks that transmit data messages between nodes and need not be described in detail for an understanding of the invention.

Each laboratory 12 of the hospital may have a laboratory computer terminal 121 connected by a laboratory node 120 to message network 19 such that laboratory 12 may exchange information with other laboratories, clinics and departments of the hospital. The hospital may also have a pharmacy 13 with a pharmacy computer terminal 131 interconnected by pharmacy node 130 with message network 19. There may also be a specimen clinic 14 having specimen computer terminals 141 for use by the specimen clinic staff and which are interconnected by specimen node 140 with message network 19.

In addition, the hospital out-patient clinic 18 may have a number of computer terminals 181, 182, 183. Computer terminals, such as out-patient clinic computer terminals 181, 182 and 183, may each be a personal computer, such as the AT&T 6300 or 3B1 Computers, provided for use by the physicians and nurses of the out-patient clinic. Each computer terminal 181, 182, 183 of outpatient clinic 18 is interconnected by out-patient node 180 to message network 19.

A record and archive department 15 of the hospital may have a number of computer terminals, such as computer terminal 151, connected to message network 19 via record node 150. The medical department of the hospital may be provided with personal computer terminals 171, 172 each connected by a medical department node 170 with message network 19. Although any computer terminal may be used to control hospital information system 1, usually one of the medical department's computer terminals, such as computer terminal 171, may be designated as a master computer terminal and used to enter record form and medical data into hospital information system 1.

Medical information system 1 may also be interconnected with various data networks by interface node 160 and interface unit 16 so that remote data base systems may be accessed to obtain current and historical medical information.

One of the main clinics of a hospital are the in-patient clinics 10 wherein medical care is provided by the patient's physician and by the physician and nursing staff of the hospital. Each of the in-patient clinic rooms or beds may be provided with a bedside computer terminal 101, 102, 103, 104 for use by the physicians and nurses attending the patient. A computer terminal such as computer terminal 101, may be a monitor terminal connected with other monitor terminals to a central computer 1000 or may be a personal computer type of computer terminal provided with the functional and operational capabilities of computer 1000. In the present embodiment of the invention, each computer terminal of medical information system 1, such as the computer terminal 101, is assumed to have the apparatus and functional operational capabilities of computer 1000.

Figure 2:
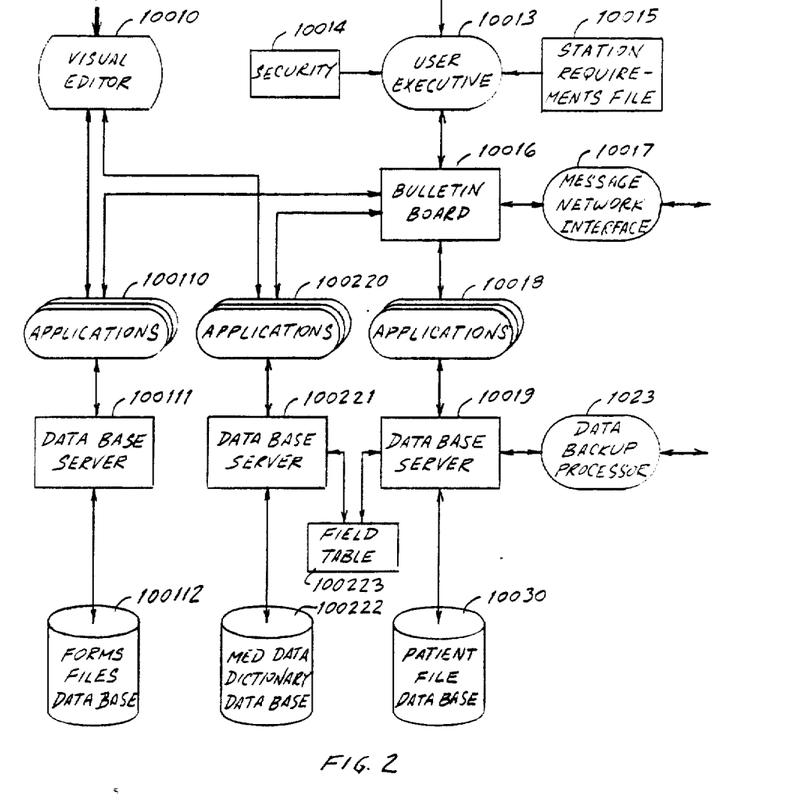
FIG. 2 is an operational chart diagram showing a functional apparatus relationship of the clinical and departmental computer terminals used in the medical information system set forth in FIG. 1.

Each computer terminal of medical information system 1 has a patient file data base 10030 for recording patient data in accordance with record and medical data recorded, respectively, in forms files data base 100112 and medical data dictionary data base 100222. A computer terminal also has a user executive 10013 in combination with security file 10014 and station requirements file data 10015. Security file 10014 is unique to each computer terminal and is intended for use in limiting access to medical information system 1 and to the patient data records in patient file data base 10030. In addition, security file 10014 restricts unauthorized user access to record and medical data recorded in forms files data base 100112 and medical data dictionary data base 100222. Security file 10014 also prevents access to applications software resident in the computer terminal and prevents unauthorized user access to message network 19.

A user defined class of computer terminals interconnected with message network 19, such as in-patient clinic 10 computer terminals 101, 102, 103, 104, 105, each have a clinical and departmental station requirements file data 10015 that define the operating characteristics of an in-patient clinic computer terminal. Station requirements file data 10015, which have clinic and department requirements data recorded therein, identifies the type of patient data that physicians and nurses may enter into or read out of the group of in-patient computer terminals 101 through 105 while administering to patients of the hospital. Another user defined class of computer terminals, for example the pharmacy computer terminals 131, may have a pharmacy station requirements file data 10015 that restricts the entry and reading of patient data to physician prescribed medications. In yet another user class of computer terminals, such as medical department 17 computer terminals 171, 172, the medical department station requirements file data 10015 may be sufficiently broad so as to enable a medical staff physician director of the hospital to use a medical department master computer terminal 171 having a broad access to patient data for consultation and diagnosis. Although any computer terminal may be designated a master computer terminal, usually a medical department computer terminal will be designated a master computer terminal wherein medical department station requirements file data 10015 will define the operational characteristics of the medical department master computer terminal. The master computer terminal controls the entry of new record and medical data into medical information system 1 and the type of record and medical data to be recorded into the forms files and medical data dictionary data bases of each computer terminal connected to message network 19.

A bulletin board 10016 located in the memory of each computer terminal identifies the types of applications software 10018 available to perform the operational characteristics required of each computer terminal. Data base server 10019 enables an authorized user of each computer terminal to access a patient file data base 10030 used to store patient data as modified by the clinical and departmental station requirements file data 10015 for each computer terminal so that modified patient data may be written into and read from a computer terminal by the authorized user of the computer terminal. Each computer terminal also has a network interface 10017 that serves to interconnect the computer terminal with a node, such as in-patient node 100, of message network 19. Large computer terminals and computers such as computers 114 and 115 of hospital financial department 11 may, FIG. 2 of the drawing, have a data backup processor link 1023 wherein data base information of the computer terminal or computer may be saved by a backup unit for security purposes to prevent loss of data.

Each clinic and department computer terminal interconnected with message network 19, FIG. 1, has a medical record subsystem 10011 and medical data subsystem 10022 used to record clinical and departmental station requirements file data 10015 modified record and medical data. Record and medical data modified by the clinical and departmental station requirement file data 10015 are filed in the forms files data base 100112 and medical data dictionary data base 100222 of each computer terminal and is used in connection with entering and reading patient data into and from a computer terminal consistent with the clinical and departmental station requirements file data 10015 modified record and medical data.

Medical record subsystem 10011, FIG. 2 of the drawing, has applications software 100110 that is identified by bulletin board 10016 and which is used in connection with data base server 100111 and forms files data base 100112 to record and read entered and verified record data. Similarly, medical data subsystem 10022 has applications software 100220 that is identified by bulletin board 10016 and which is used in connection with data base server 100221 and medical data dictionary data base 100222 to record and read entered and verified medical data. Medical data subsystem 10022 also has a field table 100223 that is used by a computer terminal in entering patient data in patient file data base 10030.

If one computer terminal, for example medical department 17 computer terminal 171, FIG. 1, has been designated as a master computer terminal, then master computer terminal 171 would be provided with a visual editor 10010 for use in entering record and medical data into medical information system 1. However, it is to be understood that each computer terminal interconnected with message network 19 may be equipped with visual editor 10010 for entering record and medical data into medical information system 1.

In the operation of a hospital, it is essential that record and medical data be constantly revised and updated to reflect changes in new medical technology. For example, new surgical, psychoanalysis and therapeutic techniques may be developed for treating patients thereby requiring changes in the format of patient records and additions to and deletions from medical data recorded in a hospital medical information system. The computer terminals of medical information system 1, FIG. 1, are arranged such that record and medical data may be entered into medical information system by the use of visual editor 10010 of a computer terminal, such as medical departmental master computer terminal 171, to condition other computer terminals. Applications software 100110 and 100220, FIG. 2, record the entered record and medical data, via the use of data base servers 100111 and 100221, in forms files data base 100112 and medical data dictionary data base 100232, respectively.

Applications software 10018 accesses the record and medical data recorded in forms files and medical data dictionary data bases 100112, 100222, via bulletin board 10016 and data base servers 100111, 100221, at predetermined intervals of time. Newly recorded record and medical data are formatted by applications software 10018 into record and medical data messages that are transmitted, via network interface 10017 and message network 19, FIG. 1, to each of the medical information system computer terminals.

When the transmitted record and medical data is received at a computer terminal, for example in-patient clinic computer terminal 101, via network interface 10017, FIG. 2, applications software 10018 modifies the received record and medical data in accordance with the in-patient clinic station requirements file data 10015. The modified record and medical data is then recorded, via applications software 10018, bulletin board 10016, applications software 100110, 100220 and data base servers 100111, 100221, in forms files data base 100112 and medical data dictionary 100222, respectively.

User executive 10013 enables patient data to be entered into a computer terminal such as in-patient clinic commuter terminal 101. Applications software 10018 reads the modified record and medical data recorded in forms files and medical data dictionary data bases 100112, 100222, via data base servers 100111, 100221, applications software 100110, 100220 and bulletin board 10016. The entered patient data is modified and then recorded, via data base server 10019, in patient file data base 10030 consistent with the in-patient clinic station requirements file data modified record and medical data.

Referring to FIGS. 3, 4, 5 and 6 of the drawing, the method of operation enables medical information system 1 to condition interconnected clinic and department computer terminals to accept patient data. The method comprises the steps 301, 302 of enabling a user 30 of a computer terminal, such as medical department master computer terminal 171, to enter records and medical data, via visual editor 10010, into computer terminal 171 and verify accuracy of the entered record and medical data. Applications software 100110, 100220 accomplishes the steps 303, 304, 305, 401, 402, 403, 404 of recording the entered and verified record and medical data in forms files and medical data dictionary data bases 100112, 100222 by determining if the entered data is record or 5 medical data and then writing the entered record and medical data, via data base servers 100111, 100221, into forms files and medical data dictionary data bases 100112, 100222, respectively, of the computer terminal.

Figure 3:
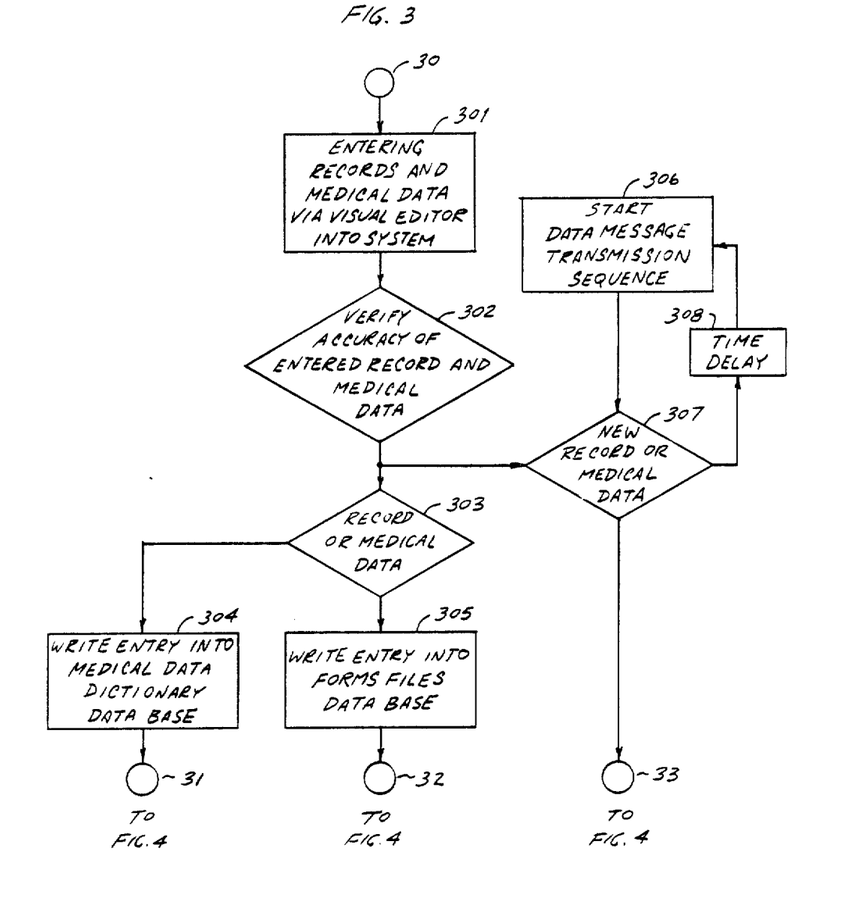
FIGS. 3, 4, 5 and 6 illustrates a flow chart of the operation of the medical information system and computer terminals set forth in FIGS. 1 and 2, respectively.
Figure 4:
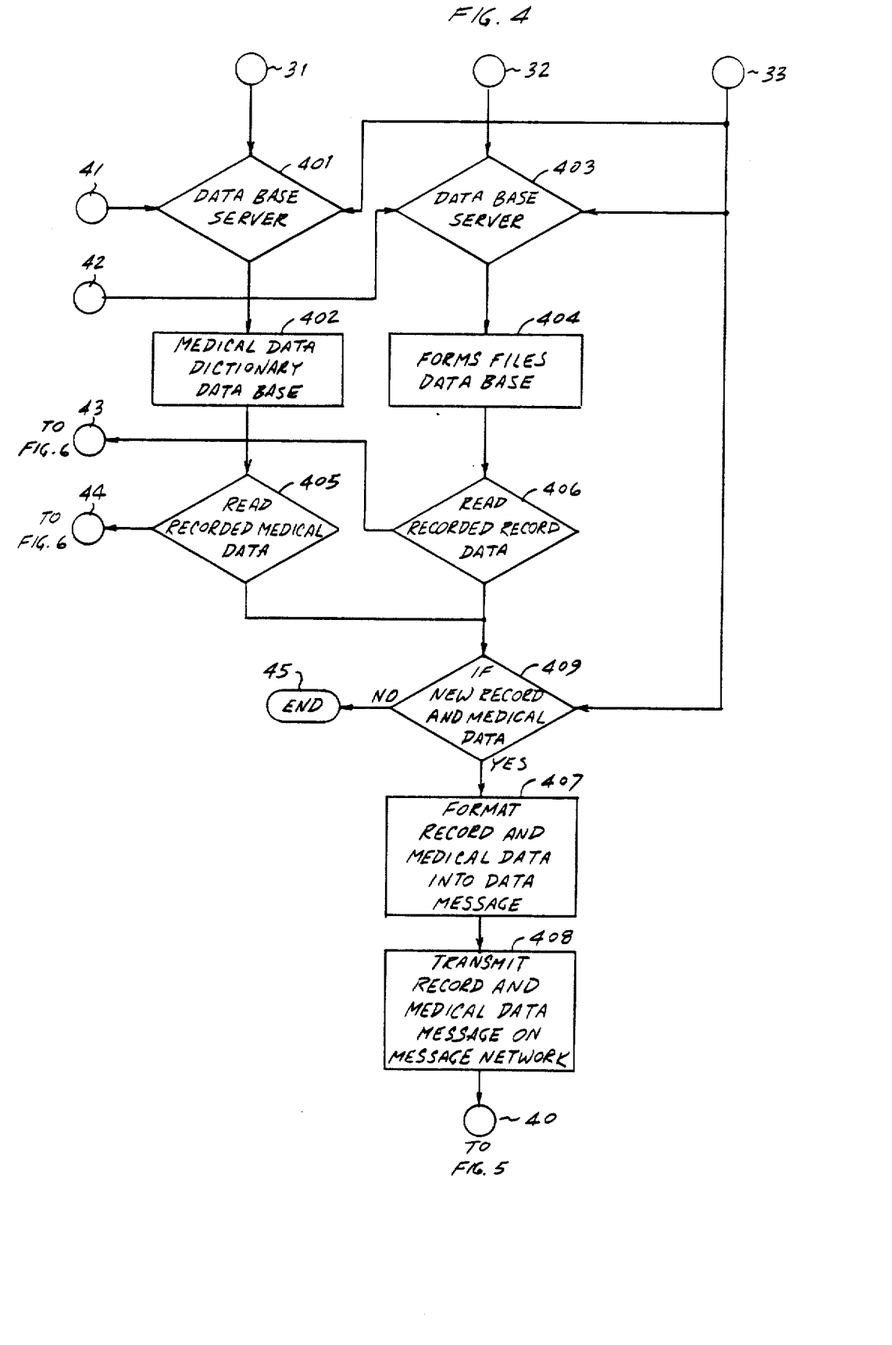

Each computer terminal or master medical department computer terminal 171 has applications software 10018 that starts a data message transmission sequence 306 to transmit new record and medical data over message network 19 to each computer terminal of medical information system 1. Start data message transmission sequence 306 operates at predetermined intervals of time defined by time delay 308, or on demand, to initiate the sequence of conditioning computer terminals of medical information system 1. If new record or medical data has been entered into the computer terminal, forms files and medical data dictionary data bases 100112, 100222 are accessed at steps 307, 401, 402, 403, 404, 405, 406, via data base servers 100111, 100221, to read the recorded record and medical data. If the accessed record and medical data is not new, than the computer terminal ends the transmission sequence at steps 45 and 409. When new record and medical data has been entered into the computer terminal, steps 407 and 408 format the record and medical data into a data message which is transmitted on message network 19 to each clinic and department computer terminal.

Figure 5:
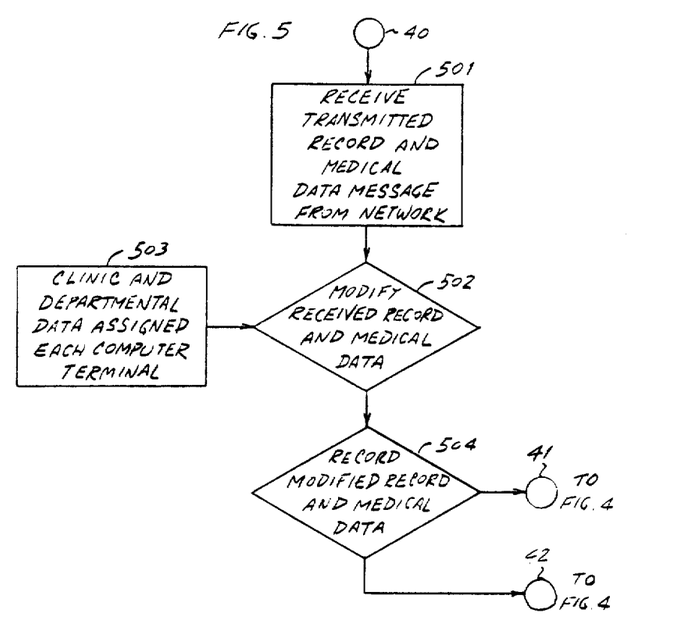
Figure 6:
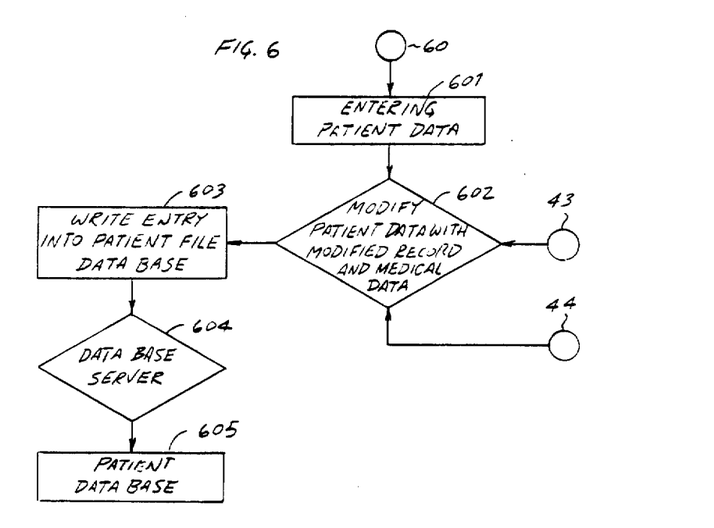

Each clinic and department computer terminal at steps 501, 502, 503 receives the transmitted record and medical data message from message network 19 and modifies the received record and medical data in accordance with the clinical and departmental station requirements file data 10015 assigned each user group of computer terminals. The modified record and medical data is recorded at steps 401, 402, 403, 404, 504, via data base servers 100111, 100221, into the forms files and medical data dictionary data bases 100112, 100222 of each receiving clinic and department computer terminal.

A user 60 located at any of the clinic and department computer terminals, for example, a physician or nurse user of in-patient clinic computer terminal 102, enters at step 601 patient data by user executive 10013, FIG. 2, into computer terminal 102. Applications software 100110, 100220 enables data base servers 100111, 100221 at steps 402, 404, 405, 406, 602, to read recorded record and medical data, FIGS. 3, 4, 5 and 6, from forms files and medical data dictionary data bases 100112, 100222 and modify the entered patient data with clinic and department station requirement file data 10015 modified record and medical data. At steps 603, 604, 605, the entered patient data is recorded by writing an entry, via data base server 10019, into patient file data base 10030 so that the patient data recorded in the computer terminal patient file data base 10030 is consistent with the modified record and medical data recorded in the receiving clinic and department computer terminal forms file and medical data dictionary data bases 100112 and 100222, respectively.

SUMMARY

It is obvious from the foregoing that the facility, economy and efficiency of a hospital may be substantially enhanced by a medical information system for use in interconnecting the clinics and departments of a hospital. It is further obvious that a medical information system wherein medical and patient data may be entered into the system and made available to all interconnected clinics and departments of a hospital in accordance with each specific clinical and departmental user, security station requirements for protecting the medical and patient data improves the efficiency and operation of the hospital.

While the instant invention has been disclosed within a hospital environment, it is to be understood that such an embodiment is intended to be illustrative of the principles of the invention and that numerous other arrangements may be devised by those skilled in the art without departing from the spirit and scope of the invention.

For example, the disclosed medical information system could be used in business applications Wherein user groups of interconnected computer terminals may be conditioned by user protocols to condition each computer terminal in accordance with user class data to display and record data.

What is claimed is:

1. A computer information system (1) having a plurality of interconnected computer terminals (1000) each defined by a user class (10015):
   characterized in that
   said information system comprises
   means (19, 10010, 10011, 10018, 10022) for entering a user information into a computer terminal for transmission to each other computer terminal,
   means (10011, 10015, 10018, 10022) for modifying said user information each receiving computer terminal to conform to said user class assigned the receiving computer terminal, and
   means (10011, 10013, 10014, 10015, 10022, 10030) for recording and displaying data entered at the receiving computer terminal in accordance with the receiving computer terminal defined user class and modified user information.

2. A medical information system (1) having a plurality of interconnected computer terminals (1000) each defined by station requirements file data (10015):
   characterized in that
   said medical information system comprises
   means (10010, 10011, 10022) for entering record and medical data into one of the computer terminals and recording said record and medical data in forms files and medical data dictionary data bases (100112, 100222) of the computer terminal,
   means (19, 10011, 10017, 10018, 10022) for accessing said recorded record and medical data at predetermined intervals of time and transmitting said accessed record and medical data to each of the interconnected computer terminals, and
   means (10011, 10013, 10014, 10018, 10022) for modifying said transmitted record and medical data at each computer terminal in accordance with the computer terminal station requirements file data and recording said modified record and medical data in the computer terminal forms files and medical data dictionary data bases (100112, 100222) for use in entering patient data into a patient file data base (10030) of the computer terminal consistent with said station requirements file data and said modified record and medical data.

3. The medical information system set forth in claim 2:
   characterized in that
   said entering recording means comprises
   visual editor means (10010) common to each of the interconnected computer terminals for entering said record and medical data into each computer terminal and for verifying the accuracy of said entered record and medical data.

4. The medical information system set forth in claim 3:
   characterized in that
   said entering and recording means comprises
   means (100110, 100220) for recording said entered and verified record and medical data into a forms files data base (100112) and medical data dictionary data base (100222), respectively, of the one computer terminal.

5. The medical information system set forth in claim 4:
   characterized in that
   said accessing and transmitting means comprises
   means (10018) for formatting said accessed record and medical data into a record and medical data message for transmission to each of the computer terminals on demand and at said predetermined intervals of time.

6. The medical information system set forth in claim 5:
   characterized in that
   said modifying and recording means comprises
   means (10017, 10018) located at each computer terminal for receiving said transmitted record and medical data message and modifying said record and medical data message in accordance with the station requirements file data assigned the receiving computer terminal.

7. The medical information system set forth in claim 6:
   characterized in that
   said modifying and recording means comprises
   means (10018, 100110, 100220) for recording said modified record and medical data into the forms files data base (100112) and medical data dictionary data base (100222), respectively, of the receiving computer terminal.

8. The medical information system set forth in claim 7:
   characterized in that
   said medical information system comprises
   means (10011, 10013, 10014, 10015, 10018, 10022) located at the receiving computer terminal for entering said patient data into the receiving computer terminal and recording said entered patient data in said patient file data base of the receiving computer terminal consistent with said modified record and medical data recorded in said receiving computer terminal forms files and medical data dictionary data bases.

9. A medical information system (1) having a plurality of computer terminals (1000) each interconnected with a network (19):
   characterized in that
   said medical information system comprises
   visual editor means (10010) common to each computer terminal for entering record and medical data into one computer terminal and for verifying the accuracy of said entered record and medical data,
   means (10011, 10022) for recording said entered and verified record and medical data into a forms files data base (100112) and medical data dictionary data base (100222), respectively, of the one computer terminal,
   means (10011, 10018, 10022) common to each computer terminal for accessing said forms files and medical data dictionary data bases and formatting said entered and verified record and medical data into record and medical data messages,
   means (10017, 10018) activated at predetermined intervals of time and on demand for transmitting said formatted record and medical data messages over the network to each of the other computer terminals connected to the network,
   means (10017, 10018) located at each computer terminal for receiving said transmitted record and medical data messages and modifying said record and medical data in accordance with station requirements file data (10015) assigned the receiving computer terminal,
   means (10011, 10022, 10018) for recording said station requirements file data modified record and medical data into a forms files data base (100112) and medical data dictionary data base (100222), respectively, of the receiving computer terminal, and means (10011, 10013, 10018, 10019, 10022) located at the receiving computer terminal for entering patient data into the receiving computer terminal and recording said entered patient data in a patient file data base (10030) of the receiving computer terminal consistent with said station requirements file data modified record and medical data recorded in said receiving computer terminal forms files and medical data dictionary data bases.

10. A hospital medical information system having a medical department master computer terminal (171) and a plurality of clinic and department computer terminals (1000) each interconnected with a message network (19):

characterized in that said hospital medical information system comprises visual editor means (10010) located at the master computer terminal for entering record and medical data into the master computer terminal and for verifying the accuracy of said entered record and medical data, master computer terminal means (10011, 10022) for recording said entered and verified record and medical data into a forms files data base (100112) and medical data dictionary data base (100222), respectively, of the master computer terminal, master computer terminal means (10011, 10018, 10022) for accessing said master computer terminal forms files and medical data dictionary data bases and formatting said entered and verified record and medical data into record and medical data messages, master computer terminal means (10017, 10018) activated at predetermined intervals of time and on demand for transmitting said formatted record and medical data messages over the message network to each clinic and department computer terminal connected to the message network, means (10017, 10018) located at each clinic and department computer terminal for receiving said transmitted record and medical data messages and modifying said record and medical data in accordance with clinic and department data (10015) assigned the receiving clinic and department computer terminal, means (10011, 10018, 10022) located at each clinic and departmental computer terminal for recording said modified record and medical data into a forms files data base (100112) and medical data dictionary data base (100222), respectively, of the receiving computer terminal, and means (10011, 10013, 10018, 10019, 10022) located at the receiving clinic and department computer terminal for entering patient data into the receiving clinic and department computer terminal and recording said entered patient data in a patient file data base (10030) of the receiving clinic and department computer terminal consistent with said modified record and medical data recorded in said receiving clinic and department computer terminal forms files and medical data dictionary data bases.

11. A method of enabling a medical information system (1) having a plurality of interconnected computer terminals (1000) for conditioning the computer terminals to accept patient data:

characterized in that said method comprises the steps of entering (301, 302) record and medical data into one of the computer terminals and recording (303, 304, 305, 401, 402, 403, 404) said record and medical data in forms files and medical data dictionary data bases of the computer terminal, accessing (306, 307, 308, 401, 402, 403, 404, 405, 406, 409) said recorded record and medical data at predetermined intervals of time and on demand and transmitting (407, 408) said accessed record and medical data to each of the interconnected computer terminals, and modifying (501, 502 503) said transmitted record and medical data at each computer terminal in accordance with station requirement data assigned the computer terminal and recording (401, 402, 403, 404, 504) said modified record and medical data in the computer terminal forms files and medical data dictionary data bases for use in entering patient data into a patient file data base of the computer terminal consistent with said station requirement data and said recorded modified record and medical data.

12. The medical information system enabling method for conditioning interconnected computer terminals to accept patient data set forth in claim 11:

characterized in that said entering and recording step comprises the steps of exercising (301) a visual editor common to each of the interconnected computer terminals for entering said record and medical data into each computer terminal and for verifying (302) the accuracy of said entered record and medical data, and recording (303, 304, 305, 401, 402, 403, 404) said entered and verified record and medical data into a forms files data base and medical data dictionary data base, respectively, of the one computer terminal.

13. The medical information system enabling method for conditioning interconnected computer terminals to accept patient data set forth in claim 12:

characterized in that said accessing and transmitting step comprises the steps of formatting (405, 406, 407, 409) said accessed record and medical data into record and medical data messages, and transmitting (408) said formatted record and medical data messages to each of the computer terminals at said predetermined intervals of time.

14. The medical information system enabling method for conditioning interconnected computer terminals to accept patient data set forth in claim 13:

characterized in that said modifying and recording step comprises the steps of receiving (501) at each computer terminal said transmitted record and medical data messages, and modifying (502, 503) said record and medical data in said record and medical data messages in accordance with said station requirement data assigned the receiving computer terminal.

15. The medical information system enabling method for conditioning interconnected computer terminals to accept patient data set forth in claim 14:

characterized in that said modifying and recording step further comprises the steps of recording (401, 402, 403, 404, 504) said station requirement modified record and medical data into a forms files data base and medical data dictionary data base, respectively, of he receiving computer terminal, and entering (601) said patient data into the receiving computer terminal and recording (402, 403, 404, 405, 406, 602, 603, 604, 605) said entered patient data in said patient file data base of the receiving computer terminal consistent with said station requirement modified record and medical data recorded in said receiving computer terminal forms files and medical data dictionary data bases.

16. A method of enabling a hospital medical information system (1) having a medical department master computer terminal (171) and a plurality of clinic and departmental computer terminals (1000) each interconnected with a message network (19) for conditioning the clinic and departmental computer terminals to accept patient data:

characterized in that said method comprises the steps of entering (301) record and medical data into the master computer terminal and verifying (302) the accuracy of said entered record and medical data, recording (304, 305, 401, 402, 403, 404) said entered and verified record and medical data in a forms files data base and medical data dictionary data base, respectively, of the master computer terminal, accessing (306, 307, 308, 401, 402, 403, 404, 405, 406, 409) said master computer terminal forms files and medical data dictionary data bases and formatting (407) said entered and verified record and medical data into record and medical data messages, transmitting (408) said formatted record and medical data messages over the message network to each clinic and department computer terminal connected to the message network, receiving (501) said transmitted record and medical data messages at each clinic and department computer terminal and modifying (502, 503) said record and medical data in accordance with clinical and departmental data assigned the receiving clinic and department computer terminal, recording (401, 402, 403, 404, 504) said modified record and medical data into a forms files data base and medical data dictionary data base, respectively, of the receiving clinic and department computer terminal, and entering (601) patient data into each receiving clinic and department computer terminal and recording (402, 404, 405, 406, 602, 603, 604, 605) said entered patient data in a patient file data base of the receiving clinic and department computer terminal consistent with said modified record and medical data recorded in said receiving clinic and department computer terminal forms files and medical data dictionary data bases.

* * * * *